United States Patent [19]

Nyman et al.

[11] 4,108,171
[45] Aug. 22, 1978

[54] BREATHING APPARATUS

[76] Inventors: Roland John Nyman, 59, 16th St., Parkhurst, Johannesburg, Transvaal Province; Johann George van der Walt, 74 Rose St., Riviera, Pretoria, Transvaal Province, both of South Africa

[21] Appl. No.: 694,451

[22] Filed: Jun. 9, 1976

[30] Foreign Application Priority Data

Jun. 11, 1975 [ZA] South Africa ............... 75/3762

[51] Int. Cl.² ........................................... A62B 7/00
[52] U.S. Cl. ........................................... 128/142.2
[58] Field of Search ............ 128/142 R, 142.2, 142.3, 128/142.5, 142.7, 145.6, 145.7, 145.8, 146.5, 147, 202, 191 R, 203; 114/319, 338, 342, 16 A, 16 E, 16.4; 61/70 R, 71 R; 73/27 R

[56] References Cited

U.S. PATENT DOCUMENTS

| 2,428,451 | 10/1947 | Emerson | 128/145.7 |
|---|---|---|---|
| 3,269,129 | 8/1966 | Zambrano | 61/70 |
| 3,436,777 | 4/1969 | Greenwood | 9/342 |
| 3,441,964 | 5/1969 | Koch et al. | 9/338 |
| 3,605,418 | 9/1971 | Levine | 114/16 E |
| 3,827,432 | 8/1974 | Lundgren et al. | 128/142.2 |
| 3,866,253 | 2/1975 | Sinks et al. | 128/142 R |
| 3,913,576 | 10/1975 | Martin et al. | 128/142.2 |
| 3,947,906 | 4/1976 | McLane | 114/16 E |

FOREIGN PATENT DOCUMENTS

| 298,016 | 7/1913 | Fed. Rep. of Germany | 128/191 R |
|---|---|---|---|
| 165 of | 1913 | United Kingdom | 128/191 R |

Primary Examiner—Robert W. Michell
Assistant Examiner—Henry J. Recla
Attorney, Agent, or Firm—McLean, Boustead and Sayre

[57] ABSTRACT

Breathing apparatus is disclosed in which a selected portion of each exhalation is returned to the inlet side for rebreathing. The percentage of each exhalation rebreathed varies from exhalation to exhalation and is determined in accordance with the detected magnitude of the preceding inhalation. Breathing mixture is withdrawn by the user from a reservoir which is in communication with a cylinder having a spring loaded piston therein. The pressure in the reservoir, and hence in said cylinder, at the end of each inhalation determines the position of the piston. A chamber receives the exhaled breath and expands to a degree dependant on the position of the piston. Once the chamber has expanded to the maximum extent permitted for that exhalation, the remainder of the exhalation is discharged from the apparatus.

12 Claims, 4 Drawing Figures

BREATHING APPARATUS

This invention relates to breathing apparatus.

It is well known that, during the normal human breathing cycle, the atmospheric air inhaled contains approximately 21% oxygen and 79% nitrogen whereas, when this air is breathed out, approximately 4% of the oxygen has been absorbed and replaced by 4% carbon dioxide. It is also common knowledge that the proportion of carbon dioxide to oxygen during the initial part of an exhalation is different from the proportion of these two gases during the latter part of an exhalation. This is because the human respiratory system has so-called dead spaces such as the mouth, nasal passages, trachea and bronchi which do not take part in the process which results in oxygen being replaced by carbon dioxide. Air which has held in these dead spaces at the end of inhalation is exhaled substantially free of carbon dioxide. Furthermore, in that portion of each exhaled breath which is carbon dioxide laden, the proportion of carbon dioxide to oxygen steadily increases. Thus the bulk of the exhaled carbon dioxide is to be found in the latter part of the exhaled breath. It is generally accepted that the carbon dioxide free portion of each exhalation constitutes about 10% of the total volume.

it is also well known that the inherent resistance of any breathing apparatus leads to a change in the user's breathing pattern. Usually the frequency of respiration drops and the so-called tidal volume increases. One of the consequences of this change in pattern, and this is not as well known as the facts set out above, is to increase the proportion of each breath which can be considered to be carbon dioxide free from approximately one tenth to approximately one third.

The present invention seeks to provide a breathing apparatus which can be used in the atmosphere or under water, and which functions in a manner compatible with the psysiological requirements of the human respiratory system.

According to the present invention there is provided breathing apparatus in which a portion of each exhalation is returned to the inlet side of the apparatus for re-breathing and the remainder of each exhalation is discharged from the apparatus, the portion of each exhalation retained for rebreathing being the part thereof which is first exhaled and the magnitude of said portion of each exhalation which is retained for re-breathing being proportional to the magnitude of the preceding inhalation.

In the preferred form, the apparatus comprises a variable volume chamber for receiving said portion of each exhalation, means for detecting the magnitude of each inhalation, and means for varying the maximum volume to which said chamber can expand during each exhalation in dependence on the detected magnitude of the preceding inhalation. In this form, there can be a normally closed shunt valve arranged to open and discharge said remainder of each exhalation upon the pressure on the outlet side of the apparatus increasing when said chamber attains its maximum permitted volume. Said normally closed valve preferably forms part of the mouthpiece of the apparatus.

A reservoir can be provided for receiving breathing mixture from a supply of breathing mixture, there being stop means for limiting the maximum volume to which said chamber can expand, and means for setting the position of said stop means in dependence on the pressure existing in said reservoir at the end of each inhalation.

In a specific constructional form said means for setting the position of the stop means comprises a cylinder in communication with said reservoir, and a piston in the cylinder, said piston being displaceable in one direction by pressure in said cylinder and in the opposite direction by spring means. A further breathing mixture reservoir can be provided for receiving breathing mixture from said supply, there being a normally closed valve between said further reservoir and said cylinder, this valve being of the demand type and opening upon the user of the apparatus commencing to inhale, a non-return valve for permitting flow in the direction from said cylinder and further reservoir to the first mentioned reservoir, and a further non-return valve between said supply and said further reservoir. Furthermore, a pressure actuated valve may be provided between said supply and said reservoirs, said pressure actuated valve being arranged to open to place the supply in communication with said reservoirs when said pressure on said outlet side increases upon the variable volume chamber attaining its maximum permitted volume.

When the apparatus is to be used underwater it can include a bouyancy bag and valve means, which valve means, when opened, permits breathing mixture to flow to said bag thereby to enable the user to increase his buoyancy. This valve means can comprise a valve closure element and spring means for unseating said element against the action of supply pressure which pressure tends to seat the element and close the valve, the arrangement being such that said valve means opens to permit breathing mixture flow to said bouyancy bag upon supply pressure dropping below a predetermined level.

The apparatus, in its underwater form, can further include an inflatable bag having a curred portion for extending around the diver's neck and two limbs which extend downwardly one on each lateral side of the diver's chest, closure means encircling each of said limbs and releasably holding said limbs in a collapsed condition and inlet valve means for supplying breathing mixture under pressure to said inflatable bag. A hose can lead from said inflatable bag, and there can be a mouthpiece at the free end of said hose.

The bouyancy bag and inflatable bag can be of substantially identical shape with the inflatable bag contained within the buoyancy bag.

For a better understanding of the invention, and to show how the same may be carried into effect, reference will now be made, by way of example, to the accompanying drawings in which.

Figure 1:
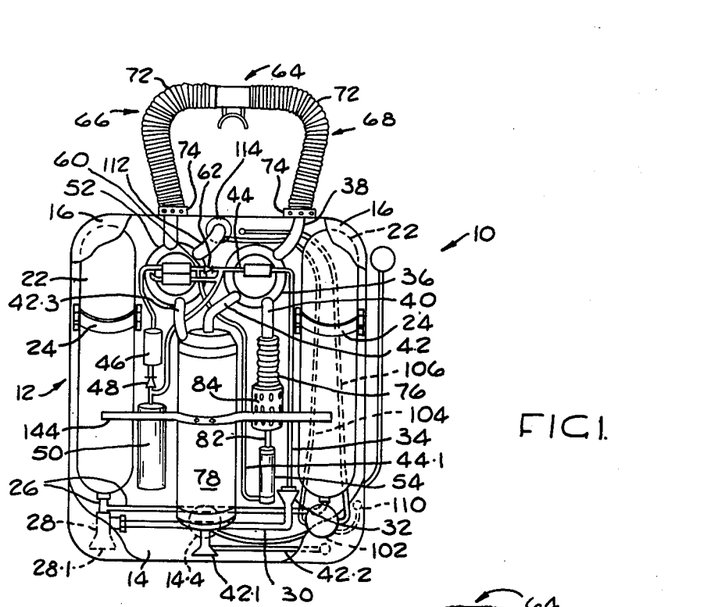
FIG. 1 is a rear elevation of a semi-open breathing apparatus in accordance with the present invention.
Figure 2:
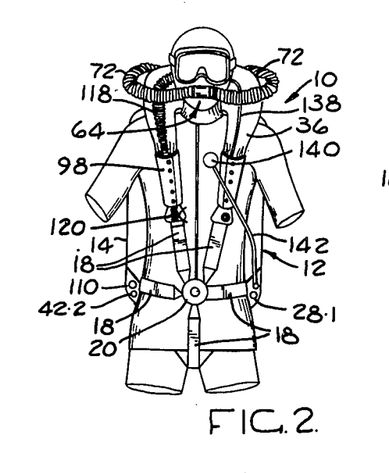
FIG. 2 is a front elevation showing the breathing apparatus of FIG. 1 being worn.
Figure 3:
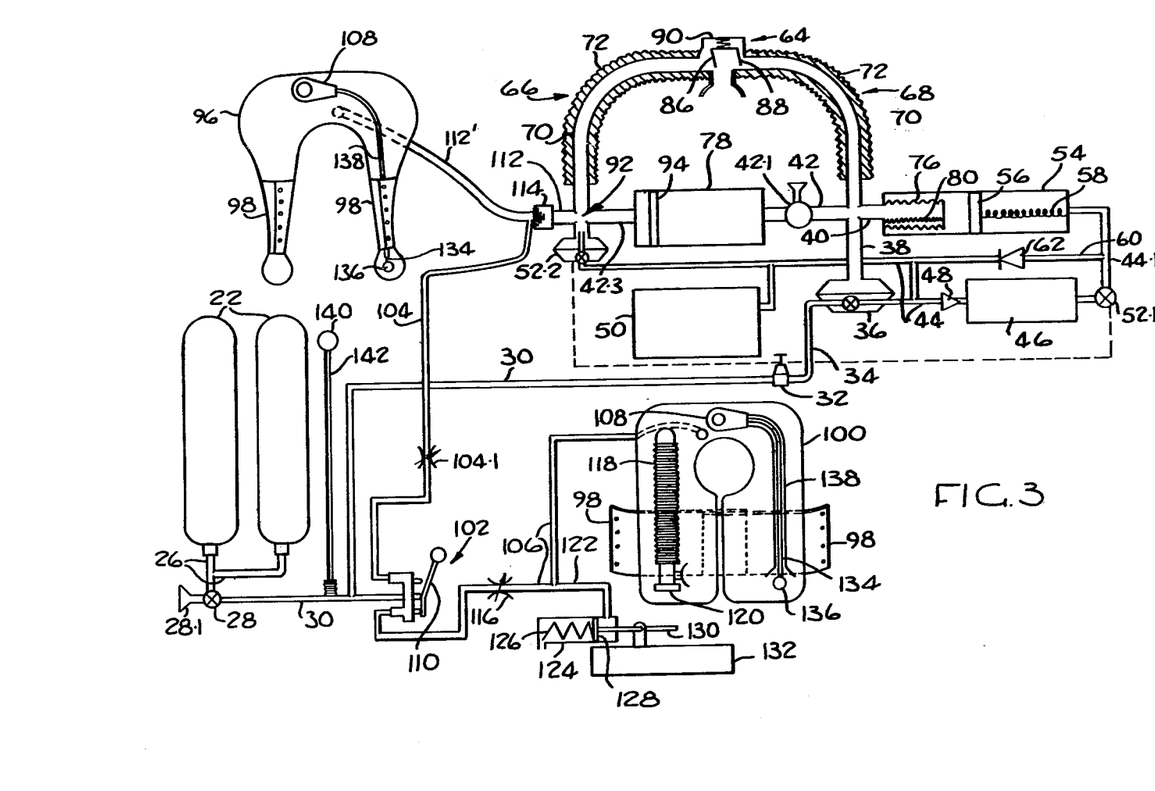
FIG. 3 is a schematic layout of the breathing apparatus of FIGS. 1 and 2.

Referring firstly to FIGS. 1 to 3, the breathing apparatus illustrated is generally designated 10 and is of the type used underwater. The apparatus comprises a body 12 consisting of a base plate 14 shaped so that it can seat comfortably on the back of the user, and a transparent cover 16 which is partially shown in FIG. 1. The base plate 14 and cover 16 can have compatible rim formations which snap-engage one another to hold the cover 16 in place with respect to the base plate 14 thereby to form an enclosed, streamlined space in which the bulk of the components of the breathing circuit are housed. This space is, however, not watertight and consequently there is no bouyancy effect tending to lift the breathing apparatus from the diver's back.

The lower corners of the base plate are offset rearwardly with respect to the remainder of this plate. As will be described, various controls are located in the recesses thus provided and are easily accessible by the diver when he is wearing the apparatus.

Five straps 18 (see FIG. 2) are attached to the base plate 14. Two of these straps are attached to the upper edge of the base plate and serve as shoulder straps and the remaining three are attached in the region of the lower edge of the base plate, two serving as waist straps and one as a crutch strap. The buckle 20 of the quick release type such as is found on parachute harnesses is connected to one of the waist straps and includes sockets for each of the other four straps.

Referring now specifically to FIGS. 1 and 3, the breathing circuit comprises a pair of cylinders 22 for containing compressed air, helium oxygen or other suitable breathing mixture. The air cylinders are releasably secured by straps 24 to the base plate 14. Outlet pipes 26 lead from the cylinders 22 to a main shut-off valve 28 by means of which the breathing mixture supply can be switched on or off. This valve is operated by a knob 28.1 located in one of the recesses of the plate 16.

A high pressure feed line 30 leads from the valve 28 to a pressure reducing valve 32. By way of example, the valve 32 can be set so as to close when the pressure on the downstream side thereof reaches, say, 800 kPa.

Downstream of the valve 32 there is an intermediate pressure feed line 34 which leads to a pressure actuated valve 36. Such valves are well known in the art and their opening and closing cycle is controlled by the breathing cycle of the user. This valve closes when the downstream pressure reaches a predetermined value and, being of a flip-flop type, does not re-open when downstream pressure falls. It will be seen from FIG. 1 that the valve 36 has three hoses 38, 40 and 42, the intermediate pressure feed line 34 and an outlet line 44 connected thereto. The line 44 leads to a reservoir 46 via a non-return valve 48 and to a larger reservoir 50. The opening and closing cycle of the valve 36 depends on the pressure changes which occur in the hose 38.

A demand valve 52 is arranged alongside the valve 36. The demand valve 52 is of a dual circuit type and is capable of controlling two lines along which breathing mixture flows. In FIG. 3 the demand valve 52 has been shown as comprising two parts 52.1 and 52.2. The interrelation between these parts will be described in more detail hereinafter. The valve part 52.1 controls flow of breathing mixture along a line 44.1 from the reservoir 46 to a chamber 54 which is in the form of a cylinder. In the schematic layout of FIG. 3 a piston 56 is shown in the cylinder constituting the chamber 54 and a tension spring 58 is provided for drawing the piston 56 towards the position in which the volume of the chamber 54 is at a minimum. A feed line 60 is shown in FIG. 3 which extends from a point between the demand valve part 52.1 and the chamber 54 to the reservoir 50, there being a non-return valve 62 in the line 60.

The mouthpiece of the apparatus is shown at 64 and is connected by flexible inlet and exhaust hoses 66 and 68 to the demand valve part 52.2 and the pressure actuated valve 36 respectively. In the form illustrated each hose 66 and 68 includes an internal hose 70 and an outer corrugated hose 72. Flow of breathing mixture to and from the mouthpiece 64 takes place through the hoses 70 which are protected by the outer hoses 72. When, as will be explained, a shunt valve of the mouthpiece 64 opens, air exhaled by the diver enters the annular gap between the inner and outer hoses 70 and 72 and eventually escapes through a series of ports 74 (see FIG. 1) provided where the outer hoses 72 are connected to the base plate 14.

The hoses 38, 40 and 42 referred to above connect the valve 36 with the mouthpiece 64, with a variable volume chamber 76 and with a canister 78 containing crystals for absorbing carbon dioxide from the exhaled breathing mixture. From FIG. 1 it will be seen that the hose 38 is simply that portion of the hose 70 which is external of the hose 72. The chamber 76 is constituted by a bellows which is uged towards its collapsed condition by a weak spring 80. One of the characteristics of the bellows shown is that its volume is directly proportional to its length. In the schematic layout of FIG. 3 the bellows is shown co-operating directly with the piston 56. However, it is more practical, as illustrated in FIG. 1, for a piston rod 82 to be connected to the piston 56 and protrude from the chamber 54. A perforated cage 84 is connected to the rod 82 and is open at its upper end. The bellows constituting the chamber 76 enters the cage 84 through its open upper end. The travel of the closed end of the bellows is limited by the closed lower end of the cage 84.

An on-off valve 42.1 is shown in the hose 42 between the demand valve 36 and the canister 78 (see FIG. 3). This valve is operated by an easily accessible knob on the end of a lever 42.2. In practice, the hose 42 enters the upper end of the canister 78 co-axially and is extended downwardly therethrough by means of a tube (not shown) co-axial with the canister 78. This tube exits from the canister 78 at its lower end and enters the valve 42.1. From the valve 42.1 the exhaled breathing mixture flows upwardly into and through the canister 78 and then along a hose 42.3 to the valve 52.

The mouthpiece 64 includes three non-return valves 86, 88 and 90. The valves 86 and 88 respectively control communication between the mouthpiece 64 and the inlet and exhaust hoses 70, and the valve 90 is a shunt valve which is spring loaded to its closed position. The position of the valve 90 is chosen so as to keep the dead spaces on the outlet side of the breathing circuit as small as possible and minimize the chances of unwanted carbon dioxide being retained.

A venturi arrangement 92 is provided where the outlet from the canister 78 joins the inlet hose 70.

The operation of the breathing apparatus as thus far described will now be explained before a number of safety and life support systems embodied in the breathing apparatus are described in detail.

When the valve 28 is opened, breathing mixture flows via the reducing valve 32 to the valve 36 which, at this stage, is open. The reservoir 46 fills via the non-return valve 48 and the reservoir 50 also fills. Escape of mixture from these reservoirs is prevented by the non-return valve 62 and by the demand valve 52 both parts of which are closed at this stage.

When the driver inhales through the mouthpiece 64, the valve 86 is sucked by him to its open position and the valve 88 is sucked to its closed position. The valve 90 remains closed under the influence of its spring loading.

The resultant drop in pressure in the inlet hose 70 has the effect of opening part 52,2, and hence part 52.1, of the demand valve 52. Breathing mixture is drawn by the diver from the reservoir 50 so that the pressure in this reservoir drops. When part 52.1 of the demand valve 52 opens, breathing mixture flows from the reservoir 46 into the chamber 54 and, along the line 60 via the valve 62, to the reservoir 50. Pressure equalization in the two reservoirs and in the chamber 54 thus takes place and the final pressure is dependent on the magnitude of the breath that the diver has taken. The position of the piston 56 in the chamber 54 at the end of inhalation depends directly on this final pressure. As a consequence, the stop constituted by the piston 56 (as illustrated in FIG. 3) or the lower end of the perforated cylinder 84 as illustrated in the practical form of FIG. 1, adopts a position which is directly proportional to the magnitude of the inhalation which has just been completed.

Figure 4:
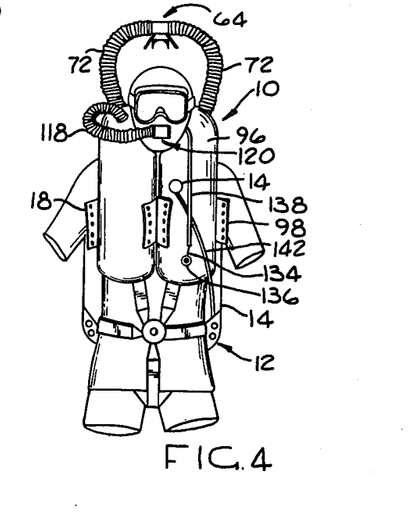
FIG. 4 is a view similar to FIG. 2 and illustrates the breathing apparatus in the condition it adopts during an emergency.

The dimensions of the reservoir 46 are chosen so that, upon demand valve part 52.1 opening, the chamber 54 is entirely filled, the piston being urged to the left as viewed in FIG. 4 to the maximum extent possible. The spring 58 ensures that the piston 56 (or cylinder 84) is withdrawn during inhalation to a position proportional to the magnitude of the inhalation, and is sufficiently strong to ensure that the piston 56 is withdrawn fully during a deep inhalation.

The demand valve 52, as it has an 'over-centre' action similar to that of the valve 36, remains open until a slight positive pressure is created in the mouthpiece whereupon it closes. Suction at the venturi 92 assists in holding the valve 52 open after an initial suction which opens the valve has been created by the diver inhaling. Immediately after the damand valve 52 closes, the valve 86 also closes. When the diver commences the exhalation portion of the respiratory cycle the valve 88 opens so that exhaled breathing mixture flows along the exhaust hose 70 to the valve 36 and chamber 76. The spring 80 offers little resistance to expansion of the chamber 76 and this expansion continues until the closed end of the chamber 76 strikes the piston 56 (as illustrated in FIG. 3) or the bottom of the perforated cylinder 84 (as illustrated in FIG. 1). As soon as the chamber 76 reaches the maximum volume that it can attain commensurate with the position in which the piston 56 (or cylinder 84) was set during the previous inhalation, a pressure build up occurs in the exhaust hose 70. This pressure is sufficient to open the demand valve 36 and also to open the non-return shunt valve 90 against the action of its spring. It will be understood that the pressure required to close demand valve 52 must be less than that required to expand the chamber 76, operate the valve 36 and open the non-return valve 90.

Immediately the valve 90 opens the remaining portion of the exhaled breathing mixture flows through the annular gaps between the hoses 70 and 72 and escapes from the apparatus through the ports 74 which are behind the diver's neck. Thus the volume of exhaled breathing mixture which the apparatus retains varies during use for, during each inhalation, the apparatus is automatically adjusted in the way described so that a appropriate volume of the subsequent exhalation is retained and the remainder dumped through the valve 90.

Actuation of the valve 36 upon expansion of the chamber 76 ceasing results in refilling of the reservoirs 46 and 50. As the demand valve 52 is closed, and the non-return valve 62 is between the valve 36 and the chamber 54, this latter chamber is isolated from the incoming breathing mixture so that the position of the piston 56 is not altered. Once the pressure in the reservoirs 46 and 50 has reached the maximum which is desired the valve 36 re-closes.

When the next inhalation commences, the positive pressure in the inlet hose 70 between the demand valve 52 and the non-return valve 86 drops and the valve 52 re-opens. The venturi arrangement provided at 92 ensures that the contents of the chamber 76 are drawn through the canister 78 and valve 42.1 into the inlet hose 70. As the pressure in the chamber 76 drops, the weak spring 80 collapses this chamber and re-setting of the position of the piston 56 takes place once more in preparation of the next exhalation portion of the respiratory cycle.

The canister 78 and the valve 42.1 can be considered as optional and a straight connection between the chamber 76 and the inlet hose 70 is possible. With this straight-through arrangement, it is essential to ensure that all the breathing mixture which contains carbon dioxide is dumped. If the canister is provided, then that portion of the exhaled breathing mixture which has a small percentage of carbon dioxide can also be retained, the carbon dioxide removed therefrom and that portion of the breathing mixture also reused.

An initial adjustment of the position which is adopted by the cylinder 84 can be undertaken before the apparatus is used. In other words, if the cylinder 84 is moved upwardly with respect to the rod 82 then automatic adjustment of the volume retained each exhalation will take place but the maximum which can be retained will be reduced for even when the piston 56 is fully retracted, the cylinder 84 will halt expansion of the chamber 76 earlier than is the case if the cylinder 84 adopts a low position on the rod 82. By fully retracting the cylinder 84 a larger volume of each exhaled breath will be retained and, in this event, it is essential that the canister 78 be provided.

It is desirable to use a container which is transparent so that colour changes of the crystals, as they become contaminated with carbon dioxide, can be noted. It is also possible to employ a canister of the type which has a barrier layer 94 which, upon contamination by carbon dioxide, changes its porous nature and prevents flow through the canister 78. Should this occur then the apparatus automatically becomes of the open circuit type and all subsequent exhaled breaths are entirely shunted through the valve 90.

The valve 42.1 has a number of functions. Firstly, it is extremely unlikely that water will ever reach the canister 78 as the apparatus always operates under positive pressure. However, should it do so harmful by-products can be formed in the canister which, in the absence of the valve 42.1, would render the entire apparatus unusable. By closing the valve 42.1, re-circulation of a retained portion of each exhalation is prevented so that the apparatus is converted into an open circuir apparatus with the canister effectively isolated. The diver can thus continue breathing normally. Furthermore, with this valve closed, the mouthpiece can be offered to another diver for use by him. This is impossible with conventional closed or semi-closed breathing circuit apparatus but can be done with the semi-open circuit of this apparatus.

Two conditions can arise which result in a build up of carbon dioxide in the breathing apparatus. Firstly, the carbon dioxide absorbant crystals may be entirely used up but the layer 94 not yet have formed a barrier. Secondly, the piston 56 may stick with the chamber 54 in its minimum volume position so that the bellows 76 operates to its maximum extent each cycle regardless of the magnitude of the previous inhalation. This condition results not only in the remaining crystals of the canister 78 being used up rapidly but also in the effect of the venturi 92 being lessened as less mixture has to be withdrawn from the reservoir 50 each inhalation. As soon as the layer 94 becomes non-porous, the venturi effect returns for no further re-circulation of exhaled mixture takes place and dumping via the valve 90 becomes pronounced. All or any of these changes can warn a diver that his apparatus is not functioning properly. If necessary, he may shut the valve 42.1, thus converting the apparatus into a normal open circuit breathing apparatus and surface using the remainder of the supply in the cylinders 22.

While intended specifically for under the use, the breathing apparatus described can be employed by fire fighters and rescue teams in atmospheres containing smoke or noxious gases. When intended specifically for underwater use, the safety and life support systems now to be described are required.

The requisite bouyancy of the apparatus is obtained by means of a horseshoe shaped bag 96 which, as shown in FIG. 2, is draped about the neck of the user and attached to the plate 14. The maximum capacity of this bag can be, for example, 20 litres but in normal use the capacity of the bag is only, say 10 litres. The difference between maximum and normal volume is achieved by 'crumpling' the depending limbs of the bag and holding them in their crumpled condition by means of cylindrical containers 98. In the preferred embodiment, each of these containers comprises a rectangular piece of material. Each piece of material is secured, along the vertical centre line thereof, to a respective one of the shoulder straps 18. The laterally projecting portions of each piece of material are free and formed in such a way that they can be releasably connected to one another to form the cylindrical containers. For example, Velcro strips or a series of pop studs can be provided. The limbs of the bag 96 can be brightly coloured and include reflective material, and the inner surfaces of the containers 98 can also be coloured and reflective. Each of the limbs of the bag 96 is also secured to a respective shoulder strap 18 so as positively to locate them regardless of whether the containers 98 are open or closed.

At the lower end of each of the depending limbs of the bag 96 there is a small drain.

Within the bag 96 there is a further bag 100, the bag 96 protecting the bag 100 against abrasion and damage. In the schematic layout of FIG. 3 the bag 100 has not been shown within the bag 96 but has been shown spaced from it as this permits all the features of the two bags readily to be illustrated. The bag 100 is substantially identical in shape to the bag 96 and its overall dimensions are sufficiently less than those of the bag 96 to enable the bag 100 to fit neatly within the bag 96. In FIGS. 3 and 4 the bag 100 is in its inflated condition and, as will clearly be seen from FIG. 4, then forms a life jacket which protrudes inwardly under the chin of the wearer to maintain his face in an upwardly facing, horizontal position when he is floating on the surface.

Supply of air to the bags 96 and 100 is controlled by a structure illustrated at 102 in FIG. 3. The structure 102 is fed from the high pressure line 30, and outlet feed lines 104 and 106 lead from the structure 102 to the bags 96 and 100 respectively. The structure 102 is formed internally with an orifice (not shown) which forms part of the communication path between the lines 30 and 104. The upstream end of the orifice is encircled by a valve seat (not shown) and a movable valve element (not shown) co-operates with this seat. The valve element is spring loaded away from the seat and inlet pressure in the line 30 acts on the movable valve element to urge it, against the action of the spring, into engagement with its seat thereby to close-off the line 104 from the line 30. By way of example, the spring can be designed so as to lift the valve closure element from its seat when the pressure in the line 30 falls to, say, 6 MPa. Thus when, during a dive, the pressure in the cylinders 22 falls to a relatively low level, the valve within the structure 102 automatically opens and permits air to flow through the line 104 and a restrictor 104.1 to the bag 96. The bag 96 thus commences to inflate and over a period of a few minutes the degree of inflation will have become such that the diver will become aware of his increase in bouyancy. This indicates to him that his breathing mixture supply has reached a level such that he must consider surfacing and he can confirm this by means of a pressure gauge 140. Should the diver be unconcious on the seabed, but maintain the mouthpiece 64 in position by means of the conventional neckstrap (not shown) and continue breathing, a situation will eventually arise where the valve in the structure 102 will open, the bag 96 will inflate, and the diver will rise to the surface automatically.

While the valve 28 is closed, the spring of the structure 102 maintains the valve closure element off its seat. As the valve 28 is opened, the pressure in the line 30 builds up and, before it reaches a pressure sufficient to close the valve of the structure 102 against spring action, breathing mixture leaks through into the line 104 and enters the bag 96. Before the diver can submerge he must deflate the bag 96 by using a dump valve 108 which will subsequently be described in more detail. Thus, prior to his dive, the operation of the valve of the structure 102 is automatically checked and the operation of the dump valve 108 must be tested by the diver.

The structure 102 further includes a three position lever 110 which can be moved from its normal position against the action of a return spring (not shown) to a second position in which it unseats the valve closure element of the structure 102. This enables the diver to increase his bouyancy when he desires. The valve closure element must, of course, be unseated against the action of the pressure in the inlet line 30 which is tending to seat the valve closure element. Over inflation of the bag 96 can be compensated for by means of the dump valve 108.

A hose 112 leads from the valve 52 to the bag 96 at the point where it and a pressure relief and non-return valve 114 are attached to the back plate 114. The hose 112' is shown in FIG. 3 only for clarity and would not normally be required in practice. The valve 114 is set to open at a pressure which is insufficient to burst the containers 98 and lower than that at which the dump valve 108 is set to open. Consequently, over inflation of the bag 96 is prevented as excess air is either fed into the breathing circuit as dumped via the valve 108.

The lever 110 of the structure 102 also controls flow of air into the line 106 which leads to the inner bag 100. The third position of the lever is provided for this purpose. Communication between the lines 30 and 106 is normally closed by a second valve closure element (not shown) and a detent mechanism (not shown) is provided which must be overcome by the force the diver exerts on the lever 110 to place these two lines in communication with one another. The detent mechanism prevents this second valve closure element re-seating unless the diver forces the lever back to its original position. Actuation of the lever 110 in this way causes breathing mixture to flow via a restrictor 116 to the bag 100 which inflates until the containers 98 open permitting the inner bag to expand the outer bag to the condition illustrated in FIG. 4. Any air in the outer bag is forced through the hose 112 to the breathing circuit and any water in the lower part of the outer bag is expelled through the bottom drains. The breathing apparatus is then in the configuration shown in FIG. 4. The coloured and/or reflective limbs of the bag 96 and the inner surface of the containers 98 are exposed in this condition.

An emergency breathing hose is shown at 118, this normally being maintained in a stored condition by being within one of the containers 98. This hose leads from the bag 100 to a mouthpiece 120. Thus the bag 100, apart from acting as a lifejacket when this is required, can also act as an emergency breathing bag. Air can be purged from the bag 100 by opening the valve of the mouthpiece 120, should the dump valve 108 have failed. The arrangement just described is such that should the main breathing circuit fail so that the diver can no longer obtain air through the mouthpiece 64, he need merely push the lever 110 against the action of the detent mechanism so as to inflate the bag 100, this action automatically freeing the hose 118 and supplying air through this hose to the mouthpiece 120. The buoyant hoses 72 and the mouthpiece 64 float upwardly to the position shown in FIG. 4 when the mouthpiece 64 is discarded in favour of the mouthpiece 120.

An auxiliary line 122 leads from downstream of the restrictor 116 to a cylinder 124. Within the cylinder 124 there is a spring 126 and a piston 128. The spring 126 holds the piston in position in which its rod 130 supports weights 132 which may be in the region of the waist of the diver. When the lever 110 is pushed to its emergency position so that the line 122 is pressurized, the piston 128 is moved against the resistance of the spring 126 so as to retract the rod 130. The weights 132 are consequently released and the effective buoyancy of the diver is increased.

It will be noted that the structur 102 is upstream of all the components of the normal breathing circuit. Thus failure of the breathing circuit will not prevent the diver obtaining an emergency breathing supply via the bag 100 and hose 118.

The dump valve 108 is a control common to the bags 96 and 100 and can be employed to dump breathing mixture from both of these bags. The dump valve 108 is connected by a cord 134 to a pull ring 136. A guide tube 138 (see particularly FIG. 4) is secured to the bag 96 and the cord 134 passes through this. The tube thus keeps the cord in place and prevents it interfering with the diver's activities.

The pressure gauge shown at 140 is mounted on the free end of a flexible pipe 142 which is screwed into a socket provided therefor.

In a preferred form of the apparatus, the air cylinders 22 are secured to the pipes 26 in a manner which makes removal thereof difficult. A filling nipple (not shown) can be provided in the region marked by the circle 14.4 in the lower part of FIG. 1. This filling nipple, which can also form the socket into which the pipe 142 is screwed, is hidden by the canister 78 which must, as a consequence, be removed before the cylinders 22 can be refilled. Furthermore, it is desirable for the canister to include a spring loaded pin which is urged to a projecting position as the canister 78 is removed. This pin is designed to make it impossible for the canister 78 to be re-mounted in its position of use until the pin has been retracted, and it is possible to arrange the contents of the canister in such a way that they must be emptied out before the user can gain access to the pin. This arrangement greatly reduces the possibility of the breathing apparatus being used with an exhausted carbon dioxide removal canister.

If the cylinders 22 are removable for filling, then a safety feature can be provided by securing a cross-bar 144 to the canister 78, the ends of this bar trapping the cylinders in place. With this arrangement the canister 78 must first be removed to permit access to be had to the cylinders. The canister can be constructed as described in the preceding paragraph.

Where the breathing apparatus is intended to be used in the atmosphere, for example, by fire fighters or rescue teams, then the buoyancy effect provided by the bag 100 is not required. However, if desired this can still be provided for use in circumstances where the breathing circuit fails to function. By actuating the lever of the structure 102 the user can by-pass the breathing circuit, expand the bag 100 and release the emergency mouthpiece 120 which he can then use until he reaches a place of safety.

The demand valve 108 can comprise two concentric seats, the inner seat being relatively resilient and the outer seat relatively hard. The central port, that encircled by the inner seat, communicates with the bag 100 and the outer, annular port communicates with the bag 96. A spring holds a flap against said seats and forms a pivot for the flap. The cord 134 is connected to the flap on the side thereof remote from the seats.

We claim:
1. Breathing apparatus comprising:
 (a) a source of breathing mixture;
 (b) inlet means for inhalation of said breathing mixture to a user and outlet means for recovering exhalation from a user;
 (c) a variable volume chamber communicating with said outlet means for receiving a portion of said each exhalation;
 (d) first flow path means from said variable volume chamber to said inlet means for returning said portion of each exhalation to said inlet means for re-breathing;
 (e) means for discharging from the apparatus the remainder of each exhalation;
 (f) normally closed valve means of the demand type having an outlet communicating with said inlet means and an inlet and including means responsive to pressure at said inlet means for opening said valve upon the user of the apparatus inhaling;
 (g) a first reservoir;

(h) a second reservoir having an inlet and an outlet;
(i) second flow path means connecting said source of breathing mixture with said first reservoir and said inlet of said second reservoir;
(j) valve means in said second flow path means for providing flow of said breathing mixture from said source to said first and second reservoirs only during exhalation by the user;
(k) non-return valve means in said second flow path means adjacent said inlet of said second reservoir preventing flow therefrom;
(l) third flow path means connecting said outlet of said second reservoir with said first reservoir and said inlet of said normally closed valve means and including further non-return valve means between said first and second reservoirs permitting flow from said second reservoir towards said first reservoir;
(m) further normally closed valve means in said third flow path means between said outlet of said second reservoir and said further non-return valve means and arranged to be opened by said means responsive to said pressure at said inlet means upon the user of the apparatus inhaling;
(n) pressure detecting means for sensing pressure in said first and second reservoirs; and
(o) stop means including means responsive to said pressure detecting means for limiting the maximum volume to which said variable volume chamber can expand during exhalation in dependence on the detected magnitude of the sensed pressure in said first and second reservoirs at the end of the preceding inhalation;
(p) whereby the volume of exhaled breathing mixture which said variable volume chamber retains is dependent upon the volume of breathing mixture inhaled.

2. Breathing apparatus according to claim 1, in which a pressure actuated valve is provided in said second flow path means between said supply and said reservoirs, said pressure actuated valve being arranged to open to place the supply in communication with said reservoirs when said pressure in said outlet means increases upon said variable volume chamber attaining its maximum permitted volume.

3. Breathing apparatus according to claim 1 and including a canister in said first flow path means for removing carbon dioxide from said portion prior to re-breathing of said portion.

4. Breathing apparatus according to claim 3 and comprising a manually operable shut-of valve in said first flow path means upstream of said canister for preventing said portion of each exhalation passing to the inlet side of the apparatus for re-breathing.

5. Breathing apparatus according to claim 1, and including an inflatable bag having a curved portion for extending around the diver's neck and two limbs which extend downwardly one on each lateral side of the diver's chest, closure means encircling each of said limbs and releasably holding said limbs in a collapsed condition and inlet valve means connected to said source of breathing mixture for supplying breathing mixture under pressure to said inflatable bag.

6. Breathing apparatus according to claim 5, and including means for supporting weights, the supporting means being arranged to release said weights upon said inlet valve means being opened to supply breathing mixture under pressure to said inflatable bag.

7. Breathing apparatus according to claim 1, and including an inflatable bag having a curved portion for extending around the diver's neck and two limbs which extend downwardly one on each lateral side of the diver's chest, closure means encircling each of said limbs and releasably holding said limbs in a collapsed condition, inlet valve means connected to said source of breathing mixture for supplying breathing mixture under pressure to said inflatable bag, a bouyancy bag, and valve means connected to said source of breathing mixture which, when opened, permits breathing mixture to flow to the bouyancy bag, said bags being of substantially identical shape with the inflatable bag contained within the buoyancy bag.

8. Breathing apparatus according to claim 7 and including a common dump valve for the buoyancy bag and the inflatable bag, the dump valve being manually operable and also being arranged to open upon the pressure in either bag exceeding a predetermined maximum, the pressure required in the buoyancy bag being less than the pressure required in the inflatable bag.

9. Apparatus as claimed in claim 1, in which said stop means is a piston in a cylinder which cylinder constitutes the detecting means, said cylinder being in communication with said second reservoir so that the pressure in said second reservoir acts on said piston to move it in one direction and there being spring means for displacing the piston in the other direction.

10. Breathing apparatus according to claim 1, and including a bouyancy bag and valve means connected to said source of breathing mixture which, when opened, permits breathing mixture to flow to said bag thereby to enable the user to increase his bouyancy.

11. Breathing apparatus according to claim 10, and including a bouyancy bag, valve means connected between a supply of breathing mixture and said bouyancy bag and a dump valve for permitting the user to discharge breathing mixture from said bag, said valve means comprising a valve closure element and spring means for unseating said element against the action of supply pressure which pressure tends to seat the element and close the valve means, the arrangement being such that said valve means opens automatically to permit breathing mixture flow to said bouyancy bag upon supply pressure dropping below a predetermined level.

12. Breathing apparatus comprising:
(a) a source of breathing mixture;
(b) inlet means for inhalation of said breathing mixture and outlet means for recovering exhalation from a user;
(c) a variable volume chamber communicating with said outlet means for receiving a portion of each exhalation;
(d) first flow path means from said variable volume chamber to said inlet means for returning said portion of each exhalation to said inlet means for re-breathing;
(e) venturi means having an outlet communicating with said inlet means and an inlet, said first flow path means communicating with said venturi means such that said portion of each exhalation is drawn from said variable volume chamber through said first flow path means to said inlet means during each inhalation;
(f) means for discharging from the apparatus the remainder of each exhalation;

(g) reservoir means and means for feeding breathing mixture from said source of breathing mixture to said reservoir means; and (h) second flow path means connecting said reservoir means to said inlet of said venturi means such that breathing mixture from said reservoir means passes through said inlet of said venturi means during each inhalation creating a negative pressure at said venturi means, said second flow path means including demand valve means responsive to pressure at said inlet means for opening said valve means in response to inhalation of the user of the apparatus and for holding open said valve means for a period after the initial inhalation of the user due to the negative pressure created by said venturi means as said breathing mixture flows through said inlet of said venturi means from said reservoir means, said valve means being adapted to close only when a positive pressure is created at said inlet means.

* * * * *

UNITED STATES PATENT AND TRADEMARK OFFICE
CERTIFICATE OF CORRECTION

PATENT NO. : 4108171
DATED : August 22, 1978
INVENTOR(S) : Roland John Nyman and Johann George van der Walt It is certified that error appears in the above-identified patent and that said Letters Patent are hereby corrected as shown below:

Column 1, line 18, "has" should read --was--;

Column 2, line 38, "curred" should read --curved--
Column 3, line 19, "The" should read --A--
Column 4, line 20, "uged" should read --urged--
Column 6, line 19, "of" (first occurrence) should read --for--;
line 45, "container" should read --canister--; line 63, "circuir" should read --circuit--
Column 7, line 25, "the" (first occurrence) should read --water-- line 63, "114" (second occurrence) should read --14--
Column 9, line 2, "as" should read --or--; line 48, "in position" should read --in a position--
Column 11, line 51, "shut-of" should read --shut-off--

Signed and Sealed this

Seventeenth Day of April 1979

[SEAL]

Attest:

RUTH C. MASON
Attesting Officer

DONALD W. BANNER
Commissioner of Patents and Trademarks